US012691204B2

(12) United States Patent
Waldfried

(10) Patent No.: US 12,691,204 B2
(45) Date of Patent: Jul. 28, 2026

(54) ADDITIVE MANUFACTURED ARTICLES HAVING PASSIVATED SURFACES AND RELATED METHODS

(71) Applicant: ENTEGRIS, INC., Billerica, MA (US)

(72) Inventor: Carlo Waldfried, Middleton, MA (US)

(73) Assignee: Entegris, Inc., Billerica, MA (US)

( * ) Notice: Subject to any disclaimer, the term of this patent is extended or adjusted under 35 U.S.C. 154(b) by 980 days.

(21) Appl. No.: 17/950,929

(22) Filed: Sep. 22, 2022

(65) Prior Publication Data

US 2023/0093910 A1     Mar. 30, 2023

Related U.S. Application Data

(60) Provisional application No. 63/336,101, filed on Apr. 28, 2022, provisional application No. 63/250,488, filed on Sep. 30, 2021.

(51) Int. Cl.
| | |
|---|---|
| *B33Y 40/20* | (2020.01) |
| *A61L 15/18* | (2006.01) |
| *A61L 17/00* | (2006.01) |
| *A61L 27/04* | (2006.01) |
| *A61L 29/02* | (2006.01) |
| *A61L 31/02* | (2006.01) |
| *B33Y 80/00* | (2015.01) |

(Continued)

(52) U.S. Cl.
CPC ............. *A61L 31/022* (2013.01); *A61L 15/18* (2013.01); *A61L 17/00* (2013.01); *A61L 27/047* (2013.01); *A61L 29/02* (2013.01); *B33Y 40/20* (2020.01); *B33Y 80/00* (2014.12); *C23C 8/08* (2013.01); *H10P 72/0402* (2026.01)

(58) Field of Classification Search
None
See application file for complete search history.

(56) References Cited

U.S. PATENT DOCUMENTS

| | | | |
|---|---|---|---|
| 5,756,222 | A | 5/1998 | Bercaw et al. |
| 5,811,195 | A | 9/1998 | Bercaw et al. |

(Continued)

FOREIGN PATENT DOCUMENTS

| | | |
|---|---|---|
| CN | 103341625 B | 5/2015 |
| CN | 109423641 A | 3/2019 |

(Continued)

OTHER PUBLICATIONS

Li Bo, 3D Printing Technology, China Light Industry Press (Chinese only), pp. 1-2, 2017.

(Continued)

*Primary Examiner* — Thaddeus B Cox

(57) ABSTRACT

Some embodiments relate to additive manufactured articles having passivated surfaces and related methods. The methods may comprise forming a three-dimensional (3D) article by additive manufacturing to obtain an additive manufactured 3D article comprising a magnesium component. The method may further comprise exposing the additive manufactured 3D article to a reactive gas phase comprising a fluorine component. The fluorine component from the reactive gas phase may react with the magnesium component of the additive manufactured 3D article to form a passivation layer at and below a surface of the additive manufacture 3D article.

13 Claims, 7 Drawing Sheets

100

102
FORMING A THREE-DIMENSIONAL ARTICLE BY ADDITIVE MANUFACTURING

104
EXPOSING THE THREE-DIMENSIONAL ARTICLE TO A REACTIVE GAS PHASE TO FORM A PASSIVATION LAYER

(51) Int. Cl.
    *C23C 8/08*       (2006.01)
    *H10P 72/00*    (2026.01)

(56)           References Cited

U.S. PATENT DOCUMENTS

| | | | |
|---|---|---|---|
| 6,215,806 B1 | 4/2001 | Ohmi et al. | |
| 7,393,765 B2 | 7/2008 | Hanawa et al. | |
| 8,293,658 B2 | 10/2012 | Shero et al. | |
| 10,913,202 B2 | 2/2021 | Espalin et al. | |
| 11,318,532 B2 | 5/2022 | Anthony et al. | |
| 11,807,946 B2 | 11/2023 | Biener et al. | |
| 2002/0104590 A1 | 8/2002 | Harenski et al. | |
| 2005/0058848 A1 | 3/2005 | Hodgens et al. | |
| 2006/0170058 A1 | 8/2006 | Chiang | |
| 2010/0080903 A1 | 4/2010 | Tamitsuji et al. | |
| 2010/0096044 A1 | 4/2010 | Misawa et al. | |
| 2013/0095380 A1 | 4/2013 | Affinito et al. | |
| 2016/0273095 A1 | 9/2016 | Lin et al. | |
| 2017/0182558 A1 | 6/2017 | Shimizu et al. | |
| 2017/0304894 A1* | 10/2017 | Buller | B22F 12/45 |
| 2017/0370005 A1 | 12/2017 | Mironets et al. | |
| 2018/0068890 A1 | 3/2018 | Zope et al. | |
| 2018/0135157 A1 | 5/2018 | Jeong et al. | |
| 2018/0202047 A1 | 7/2018 | Lin et al. | |
| 2018/0214953 A1 | 8/2018 | Knittel et al. | |
| 2019/0040529 A1 | 2/2019 | Verbaas et al. | |
| 2019/0085478 A1 | 3/2019 | Burks et al. | |
| 2019/0312202 A1 | 10/2019 | Yokoyama et al. | |
| 2020/0079966 A1 | 3/2020 | Holt et al. | |
| 2020/0254547 A1 | 8/2020 | Puidokas et al. | |
| 2020/0324470 A1 | 10/2020 | Walker | |
| 2020/0397542 A1 | 12/2020 | Andersen et al. | |
| 2021/0198788 A1 | 7/2021 | Waldfried et al. | |
| 2022/0181124 A1 | 6/2022 | Duan et al. | |
| 2022/0251699 A1 | 8/2022 | Miyaishi et al. | |
| 2023/0093910 A1 | 3/2023 | Waldfried | |
| 2024/0401197 A1 | 12/2024 | Wu et al. | |

FOREIGN PATENT DOCUMENTS

| | | | |
|---|---|---|---|
| CN | 110352106 A | 10/2019 | |
| CN | 109112595 A | 6/2020 | |
| CN | 109940163 B | 12/2020 | |
| CN | 112675362 A | 4/2021 | |
| CN | 220069926 U | 11/2023 | |
| EP | 460700 A | 12/1991 | |
| JP | S57117992 A | 7/1982 | |
| JP | H0466657 A | 3/1992 | |
| JP | H04120728 A | 4/1992 | |
| JP | H09298329 A | 11/1997 | |
| JP | 2986859 B2 | 12/1999 | |
| JP | 2003119540 A | 4/2003 | |
| JP | 2010037581 A | 2/2010 | |
| JP | 2019218620 A | 12/2019 | |
| KR | 20160145652 A | 12/2016 | |
| KR | 20230007495 A | 1/2023 | |
| TW | 202318535 A | 5/2023 | |
| WO | 2008041701 A1 | 4/2008 | |
| WO | 2019194869 A2 | 10/2019 | |
| WO | 2020014287 A2 | 1/2020 | |
| WO | 2020257488 A1 | 12/2020 | |
| WO | 2023079831 A1 | 5/2023 | |

OTHER PUBLICATIONS

Lea, C. et al., Magnesium diffusion, surface segregation and oxidation in Al—Mg alloys, Chapman and Hall Ltd., 1984.

Dong et al., Extrusion-based 3D printed magnesium scaffolds with multifunctional MgF2 and MgF2—CaP coatings, The Royal Society of Chemistry, Biomaterial Science, vol. 9, pp. 7159-7182, 2021.

* cited by examiner

FORMING A THREE-DIMENSIONAL ARTICLE BY ADDITIVE MANUFACTURING

EXPOSING THE THREE-DIMENSIONAL ARTICLE TO A REACTIVE GAS PHASE TO FORM A PASSIVATION LAYER

204

208

202

200

ADDITIVE MANUFACTURED ARTICLES HAVING PASSIVATED SURFACES AND RELATED METHODS

CROSS-REFERENCE TO RELATED APPLICATIONS

This application claims the benefit under 35 USC 119 of U.S. Provisional Patent Application No. 63/250,488, filed Sep. 30, 2021, and 63/336,101 filed on Apr. 28, 2022, the disclosure of each is hereby incorporated herein by reference in its entirety.

FIELD

This disclosure generally relates to additive manufactured articles having passivated surfaces and related methods.

BACKGROUND

Machining processes do not permit the manufacture of devices (or device parts) having complex shapes as a single component. For example, a device having a complex shape can only be manufactured by assembling multiple components. The assembly of multiple components often results in seams or welds formed at the interface of two or more components.

SUMMARY

In a first aspect a method for forming an article is disclosed including: forming a three-dimensional (3D) article by additive manufacturing to obtain an additive manufactured 3D article, wherein the additive manufactured 3D article includes a magnesium component; and exposing the additive manufactured 3D article to a reactive gas phase to form a passivation layer, wherein the reactive gas phase includes a fluorine component, wherein the fluorine component reacts with the magnesium component to form magnesium fluoride at and below a surface of the additive manufactured 3D article.

A second aspect according to the first aspect, wherein the forming includes dispensing a 3D printable material from a 3D printer to form the additive manufactured 3D article.

A third aspect according to any of the preceding aspects, wherein the magnesium component includes at least one of a magnesium-containing metal alloy, a magnesium ion, a magnesium-containing metal oxide, elemental magnesium, or any combination thereof.

A fourth aspect according to any of the preceding aspects, wherein the additive manufactured 3D article has a monolithic structure that is not capable of construction by machining.

A fifth aspect according to any of the preceding aspects, wherein the additive manufactured 3D article is an article of unitary construction.

A sixth aspect according to any of the preceding aspects, wherein the additive manufactured 3D article includes at least one of a plenum, a trench, a structure defining a hole, a structure defining a channel, a structure defining a cavity, or any combination thereof.

A seventh aspect according to any of the preceding aspects, wherein the additive manufactured 3D article has an aspect ratio of 2:1 to 1000:1, wherein the aspect ratio is a ratio of two of a width, a depth, a height, or a diameter.

An eighth aspect according to any of the preceding aspects, wherein the additive manufactured 3D article does not include seams.

A ninth aspect according to any of the preceding aspects, wherein the additive manufactured 3D article does not include braze joints.

A tenth aspect according to any of the preceding aspects, wherein the additive manufactured 3D article does not include weld joints.

An eleventh aspect according to any of the preceding aspects, wherein the reactive gas phase includes at least one of $CF_4$, $C_2F_4$, $C_3F_6$, $C_4F_8$, $CHF_3$, $C_2H_2F_2$, $C_2F_6$, HF, $CH_3F$, or any combination thereof.

A twelfth aspect according to any of the preceding aspects, wherein the reactive gas phase is derived from at least one of polymerized perfluoroalkylethylene having a $C_1$-$C_{10}$ perfluoroalkyl group; polytetrafluoroethylene (PTFE); tetrafluoroethylene/perfluoro(alkyl vinyl ether) copolymer (PFA); tetrafluoroethylene/hexafluoropropylene copolymer (FEP); tetrafluoroethylene/perfluoro(alkyl vinyl ether)/hexafluoropropylene copolymer (EPA); poly-hexafluoropropylene; ethylene/tetrafluoroethylene copolymer (ETFE); poly trifluoroethylene; polyvinylidene fluoride (PVDF); polyvinyl fluoride (PVF); polychlorotrifluoroethylene (PCTFE); ethylene/chlorotrifluoroethylene copolymer (ECTFE); or any combination thereof.

A thirteenth aspect according to any of the preceding aspects, wherein the magnesium fluoride covers at least 90% of gas-exposed surfaces of the additive manufactured 3D article.

In a fourteenth aspect a component of a semiconductor manufacturing tool is disclosed comprising an article formed according to the methods disclosed herein.

In a fifteenth aspect to a medical device is disclosed comprising an article formed according to the methods disclosed herein.

In a sixteenth aspect an article is disclosed including: an additive manufactured three-dimensional (3D) body, wherein the additive manufactured 3D body includes a magnesium component, wherein the additive manufactured 3D body has a monolithic structure that is not capable of construction by machining; and a passivation layer at and below a surface of the additive manufactured 3D body, wherein the passivation layer includes magnesium fluoride, wherein the magnesium fluoride is a reaction product of the magnesium component and a fluorine component from a reactive gas phase.

A seventeenth aspect according to the sixteenth aspect, wherein the additive manufactured 3D article includes at least one of a plenum, a trench, a structure defining a hole, a structure defining a channel, a structure defining a cavity, or any combination thereof.

An eighteenth aspect according to the sixteenth or seventeenth aspect, the additive manufactured 3D article has an aspect ratio of 2:1 to 1000:1, wherein the aspect ratio is a ratio of two of a width, a depth, a height, or a diameter.

A nineteenth aspect according to any of the sixteenth through eighteenth aspects, wherein the additive manufactured 3D article is an article of unitary construction.

A twentieth aspect according to any of the sixteenth through nineteenth aspects, wherein the additive manufactured 3D article does not include seams, does not include braze joints, and does not include weld joints.

In a twenty-first aspect, a medical device is disclosed comprising: an additive manufactured three-dimensional (3D) body, wherein the additive manufactured 3D body comprises a magnesium component; and a passivation layer at and below a surface of the additive manufactured 3D body, wherein the passivation layer comprises magnesium fluoride, wherein the magnesium fluoride is a reaction product of the magnesium component and a fluorine component from a reactive gas phase.

A twenty-second aspect according to the twenty-first aspect, wherein the medical device is configured for implantation into a mammal.

A twenty-third aspect according to the twenty-first aspect, wherein the medical device is configured for temporary insertion into a mammal.

A twenty-fourth aspect according to the twenty-first aspect, wherein the medical device is configured for external use on a mammal.

A twenty-fifth aspect according to any of the twenty-first to the twenty-fourth aspects, wherein the additive manufactured 3D body is biocompatible.

A twenty-sixth aspect according to any of the twenty-first to the twenty-fifth aspects, wherein the additive manufactured 3D body is a body of the medical device.

A twenty-seventh aspect according to any of the twenty-first to the twenty-fifth aspects, wherein the additive manufactured 3D body is a component of the medical device.

A twenty-eighth aspect according to any of the twenty-first to the twenty-seventh aspects, wherein the additive manufactured 3D body is at least one of a balloon, a graft, a stent, a catheter, a shunt, an embolic agent, a pacemaker, a defibrillator, an artificial implant, a prosthetic, a stimulator, a sensor, a wire, a lead, a valve, a plug, a pump, a filter, a mechanical connector, a tube, a plate, a surgical tool, an enclosure, any component thereof, or any combination thereof.

A twenty-ninth aspect according to any of the twenty-first to the twenty-eighth aspects, wherein the additive manufactured 3D body is at least one of an angioplasty balloon, a valvuloplasty balloon, a deployment balloon, a pacemaker lead, a prosthetic heart valve, a vascular filter, a vascular plug, an artificial heart valve, an artificial heart, a catheter tip, a suture, a surgical staple, a screw, a nail, a bracket, a pin, a rod, a fixture, a guide wire, a drug pump, a synthetic vessel graft, a vascular graft, a nonvascular graft, a stent graft, a vascular stent, a coronary stent, a peripheral stent, an intraluminal paving stent, an arteriovenous shunt, an aneurysm filler, an implantable pulse generator, an implantable cardiac defibrillator, a cardioverter defibrillator, a spinal stimulator, a brain stimulator, a sacral nerve stimulator, a bone prosthetic, a joint prosthetic, a plastic tubing, a metal tubing, a dental braces, a hearing aid, a bandage, any component thereof, or any combination thereof.

A thirtieth aspect according to any of the twenty-first to the twenty-ninth aspects, wherein the additive manufactured 3D body comprises a structure having an aspect ratio of 2:1 to 1000:1.

A thirty-first aspect according to the thirtieth aspect, wherein the aspect ratio is a ratio of two of a width, a depth, a height, or a diameter.

A thirty-second aspect according to any of the twenty-first to the thirty-first aspects, wherein the magnesium component comprises at least one of a magnesium-containing metal alloy, a magnesium ion, a magnesium-containing metal oxide, elemental magnesium, or any combination thereof.

A thirty-third aspect according to any of the twenty-first to the thirty-second aspects, wherein the additive manufactured 3D body has a monolithic structure that is not capable of construction by machining.

A thirty-fourth aspect according to any of the twenty-first to the thirty-third aspects, wherein the additive manufactured 3D body is an article of unitary construction.

A thirty-fifth aspect according to any of the twenty-first to the thirty-fourth aspects, wherein the additive manufactured 3D body does not comprise seams.

A thirty-sixth aspect according to any one of the twenty-first to the thirty-fifth aspects, wherein the additive manufactured 3D body does not comprise braze joints.

A thirty-seventh aspect according to any of the twenty-first to the thirty-sixth aspects, wherein the additive manufactured 3D body does not comprise weld joints.

A thirty-eighth aspect according to any of the twenty-first to the thirty-seventh aspects, wherein the reactive gas phase comprises at least one of $CF_4$, $C_2F_4$, $C_3F_6$, $C_4F_8$, $CHF_3$, $C_2H_2F_2$, $C_2F_6$, HF, $CH_3F$, or any combination thereof.

A thirty-ninth aspect according to any of the twenty-first to the thirty-eighth aspects, wherein the reactive gas phase is derived from at least one of polymerized perfluoroalkylethylene having a $C_1$-$C_{10}$ perfluoroalkyl group; polytetrafluoroethylene (PTFE); tetrafluoroethylene/perfluoro(alkyl vinyl ether) copolymer (PFA); tetrafluoroethylene/hexafluoropropylene copolymer (FEP); tetrafluoroethylene/perfluoro(alkyl vinyl ether)/hexafluoropropylene copolymer (EPA); polyhexafluoropropylene; ethylene/tetrafluoroethylene copolymer (ETFE); poly trifluoroethylene; polyvinylidene fluoride (PVDF); polyvinyl fluoride (PVF); polychlorotrifluoroethylene (PCTFE); ethylene/chlorotrifluoroethylene copolymer (ECTFE); or any combination thereof.

BRIEF DESCRIPTION OF THE DRAWINGS

Reference is made to the drawings that form a part of this disclosure, and which illustrate embodiments in which the materials and methods described herein can be practiced.

DETAILED DESCRIPTION

Embodiments of the present disclosure relate to, among other things, articles formed by additive manufacturing, methods for forming articles by additive manufacturing, applications involving articles formed by additive manufacturing, and related embodiments. Some embodiments of the present disclosure relate to additive manufactured articles having one or more passivated surfaces. In some embodiments, the articles formed by additive manufacturing may have at least one of a monolithic structure, one or more high aspect ratio features, or any combination thereof. In some embodiments, following fabrication of the article by additive manufacturing, the article may be subjected to a vapor-phase fluorination process in which one or more surfaces of the additive manufactured article is passivated with magnesium fluoride. In some embodiments, the vapor-phase fluorination process is sufficient to passivate all exposed surfaces of the additive manufactured articles. In some embodiments, the passivated surface(s) of the additive manufactured article provides at least one of a corrosion resistant layer, an etch resistant layer, or any combination thereof.

Figure 1:
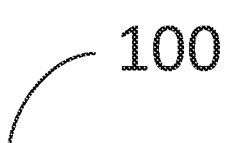
FIG. 1 is a flowchart of a method for forming an article, according to some embodiments of the present disclosure.
Figure 1:
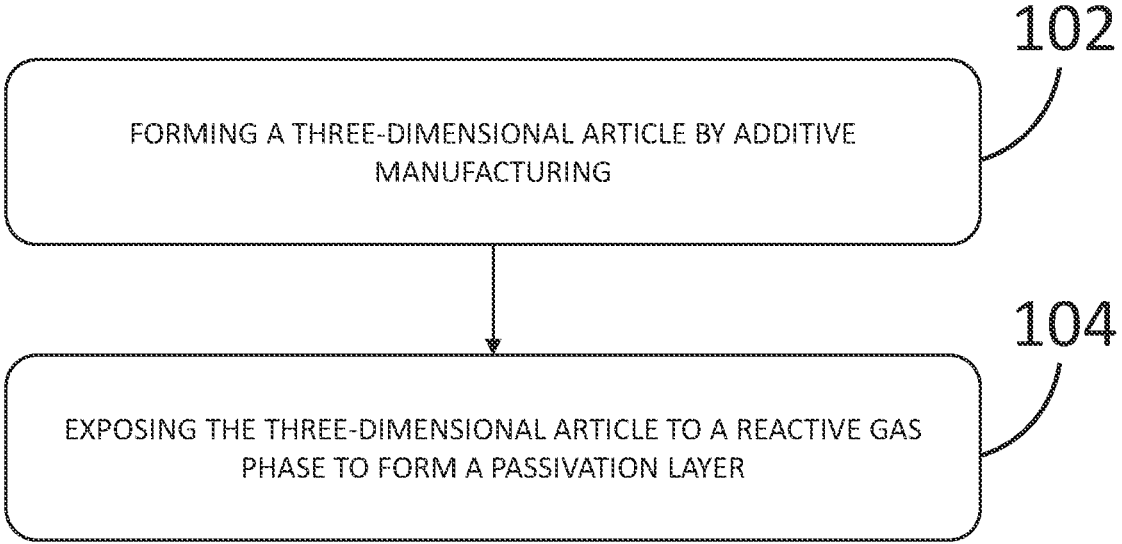

FIG. 1 is a flowchart of a method for forming an article, according to some embodiments of the present disclosure. As shown in FIG. 1, the method 100 for forming an article may comprise one or more of the following steps: a step 102 of forming a three-dimensional (3D) article by additive manufacturing and a step 104 of exposing the 3D article to a gas phase reactant to form a passivation layer.

At step 102, the method 100 may comprise forming a 3D article by additive manufacturing. In some embodiments, additive manufacturing may comprise 3D printing. In some embodiments, the 3D article is formed by dispensing a 3D printable material from a 3D printer to form the 3D article. In some embodiments, the 3D printing may comprise creating a solid object from a 3D model by building the object incrementally. In some embodiments, for example, 3D printing may comprise applying the 3D printable material in layers which are selectively joined or fused together to create a 3D article having at least one of a monolithic structure, a unitary construction, a structure not capable of construction by machining, or any combination thereof. The 3D printing may be performed using at least one of the following: selective laser melting (SLM), selective laser sintering (SLS), fused deposition modeling (FDM), electron beam melting (EBM), direct metal laser sintering (DMLS), or any combination thereof.

In some embodiments, the 3D article may be formed from a precursor material. In some embodiments, the precursor material may comprise, consist of, or consist essentially of a 3D printable material. In some embodiments, the precursor material may comprise a raw material, such as a granular raw material. For example, in some embodiments, the precursor material may comprise at least one of a metal powder, a metal alloy powder, a ceramic powder, a polymer (e.g., a photopolymer resin, a thermoplastic polymer, or any combination thereof), or any combination thereof. In some embodiments, the precursor material may comprise a material capable of being fused by heat (e.g., a scanning laser or scanning electron beam). In some embodiments, the precursor material may comprise, consist of, or consist essentially of a metal component. In some embodiments, the metal component may comprise, consist of, or consist essentially of at least one of one or more metals, one or more metal compounds, one or more metal oxides, one or more metal alloys, or any combination thereof. In some embodiments, the precursor material may comprise, consist of, or consist essentially of, or may be selected from the group consisting of, at least one of the following: Al, Mg, Ni, Ti, V, Fe, Cr, Zn, Mo, Li, Cu, Mn, In, Sn, P, Sb, As, Bi, Pb, Te, Se, W, Ge, Cd, Co, Ag, Pt, Hg, Ir, Os, S, K, Ga, Na, Nb, Ta, Si, $La_2O_3$, NiO, $Fe_2O_3$, $Al_2O_3$, BaO, MgO, CaO, $HfO_2$, $ZrO_2$, $SnO_2$, $In_2O_3$, $K_2O$, $CeO_2$, $Ce_2O_3$, $Sc_2O_3$, $Y_2O_3$, $Ga_2O_3$, $Na_2O$, $B_2O_3$, SrO, BeO, titanium oxides, tantalum oxides, niobium oxides, silicon carbide, stainless steel, rare earth oxides, a component thereof, or any combination thereof. In some embodiments, the precursor material may comprise one or more solvents.

In some embodiments, the 3D article may comprise at least a magnesium component. The magnesium component may comprise magnesium in a mobile form. For example, in some embodiments, the magnesium component may comprise magnesium in a metallic form as a metal alloy, a metal ion, a metallic oxide, elemental magnesium, or any combination thereof. In some embodiments, the magnesium component comprises at least one of a magnesium-containing metal alloy, a magnesium ion, a magnesium-containing metal oxide, elemental magnesium, or any combination thereof.

In some embodiments, the 3D article may comprise an additive manufactured 3D article. In some embodiments, the 3D article may comprise an additive manufactured 3D body. In some embodiments, the 3D article may have a monolithic structure. In some embodiments, a monolithic structure may be a structure that is not capable of construction by machining. In some embodiments, the term "machining" may refer to a process of shaping a material by, for example and without limitation, milling, drilling, grinding, cutting, carving, chipping, or forming, among other things. In some embodiments, a monolithic structure may be a structure of unitary construction. In some embodiments, the 3D article may be of unitary construction. In some embodiments, the term "unitary construction" may refer to a structure that does not comprise two or more structures joined together post-fabrication. For example, in some embodiments, the 3D article may not comprise any structures that are separately fabricated and subsequently joined together. In some embodiments, a monolithic structure of unitary construction may be at least one of a structure that does not comprise seams, a structure that does not comprise braze joints, a structure that does not comprise weld joints, or any combination thereof.

In some embodiments, the 3D article may have at least one feature. The at least one feature may comprise, consist of, or consist essentially of, or may be selected from the group consisting of, a plenum, a trench, a structure defining a hole, a structure defining a channel, a structure defining a cavity (e.g., a partially enclosed region defining a cavity), a planar surface, a non-planar surface, or any combination thereof. In some embodiments, the at least one feature may have an aspect ratio. For example, in some embodiments, the aspect ratio of a feature may refer to a ratio of a depth to a width. In some embodiments, the aspect ratio of a feature may refer to a ratio of a width to a depth. In some embodiments, the aspect ratio of a feature may refer to a ratio of two of a length, a width, or a height. In some embodiments, the aspect ratio of a feature may refer to a ratio of a depth to a diameter. In some embodiments, the aspect ratio of a feature may refer to a ratio of a diameter to a depth. In some embodiments, the aspect ratio of a feature may refer to a ratio of at least two of the following: a width, a depth, a height, a diameter, and a circumference.

In some embodiments, the at least one feature may have an aspect ratio of 2:1 to 1000:1, or any range or subrange therebetween. For example, the at least one feature may have an aspect ratio of at least 2:1, at least 3:1, at least 4:1, at least 5:1, at least 6:1, at least 7:1, at least 8:1, at least 9:1, at least 10:1, at least 15:1, at least 20:1, at least 25:1, at least 30:1, at least 35:1, at least 40:1, at least 45:1, at least 50:1, at least 55:1, at least 60:1, at least 65:1, at least 70:1, at least 75:1, at least 80:1, at least 85:1, at least 90:1, at least 95:1, at least 100:1, at least 200:1, at least 300:1, at least 400:1, at least 500:1, at least 600:1, at least 700:1, at least 800:1, at least 900:1, to 1000:1, and/or any range or subrange therebetween.

In some embodiments, the 3D article may be a component of a semiconductor manufacturing tool, such as, for example and without limitation, at least one of a process chamber, a sidewall, a flow head (e.g., a showerhead), a shield, a tray, a support, a nozzle, a valve, a conduit, a stage for handling or holding an object, a wafer handling fixture, a wafer carrier, a wafer holder, a susceptor, a spindle, a chuck, a ring, a baffle, a fastener (e.g., a (threaded) screw, a (threaded) nut, a bolt, a clamp, a rivet, etc.), a membrane, a filter, a three-dimensional network, a conduit (e.g., a gas line), a manifold (e.g., a gas manifold), a window, an injector, a liner, a manifold, or any combination thereof. The magnesium fluoride passivation layer may be biocompatible such that the 3D article may be useful as an implantable medical device or any component thereof. For example, in other embodiments, the 3D article may be a medical device or a component of a medical device, such as, for example and without limitation, at least one of a medical instrument, a medical implant, or an article having a medical use. Non-limiting examples of medical devices and/or components thereof, include at least one of prosthetics (e.g., knees, joints, shoulders, hips, etc.), dental braces, hearing aids, braces, nails, screws, plates, catheters, tubes, valves, enclosures, wires, stents, connectors, or any combination thereof, and the like.

At step 104, in some embodiments, the 3D article may be exposed to the reactive gas phase to form the passivation layer. In some embodiments, the exposing may be performed under conditions sufficient to result in formation of the passivation layer. In some embodiments, the exposing may be performed in a chamber configured to expose the reactive gas phase to the 3D article. In some embodiments, the exposing may be performed in a process chamber. In some embodiments, the exposing may be performed in a reaction vessel. In some embodiments, the exposing may be performed by vaporizing a solid or liquid precursor material to obtain the reactive gas phase. In some embodiments, the solid or liquid precursor material is vaporized in the reaction vessel or process chamber; or in a separate vessel, followed by supplying the reactive gas phase to the process chamber or the reaction vessel. In some embodiments, the exposing may be performed by supplying the reactive gas phase to the process chamber or reaction vessel (e.g., without vaporizing a solid or liquid precursor material to obtain the reactive gas phase). In some embodiments, the passivation layer is formed by a plasma-free deposition process. In some embodiments, the passivation layer is formed by a non-plasma deposition process.

In some embodiments, the reactive gas phase may comprise a fluorine component. In some embodiments, the reactive gas phase may comprise a molecular fluorine source vapor, which may be derived from a liquid or solid. In some embodiments, the fluorine component may comprise, consist of, or consist essentially of molecular fluorine. In some embodiments, the fluorine component is not ionic, substantially not ionic, not processed (e.g., by adding energy other than heat) to form plasma, or any combination thereof. In some embodiments, the fluorine component may comprise, consist of, or consist essentially of at least one of a fluorinated organic compound, a perfluorinated organic compound, or any combination thereof. In some embodiments, for example, the fluorine component may comprise, consist of, or consist essentially of at least one of a fluorinated alkane, a perfluorinated alkane, a fluorinated alkene, a perfluorinated alkene, or any combination thereof, wherein any one or more of which may be linear or branched. In some embodiments, the fluorine component may comprise, consist of, or consist essentially of, or may be selected from the group consisting of, at least one of $CF_4$, $C_2F_4$, $C_3F_6$, $C_4F_8$, $CHF_3$, $C_2H_2F_2$, $C_2F_6$, HF, $CH_3F$, or any combination thereof. In some embodiments, the reactive gas phase is distinct from plasma, processes for generating plasma, or any combination thereof.

In some embodiments, the reactive gas phase may comprise a gaseous fluorinated polymer derived from a non-gaseous fluorinated polymer (e.g., a solid or a liquid phase fluorinated polymer). In some embodiments, the fluorinated polymer may be a homopolymer or a copolymer. In some embodiments, the fluorinated polymer may comprise a copolymer of at least one fluoroolefin monomer and optionally at least one non-fluorinated co-monomer. In some embodiments, the fluorinated polymer may be fluorinated (i.e., partially fluorinated), perfluorinated, or may include non-fluorine halogen atoms, such as, for example and without limitation, chlorine. In some embodiments, a molecular fluorine source may be liquid or solid at room temperature, but that vaporizes at the process temperatures disclosed herein. Non-limiting examples of fluoropolymers include, without limitation, at least one of the following: polymerized perfluoroalkylethylene having a $C_1$-$C_{10}$ perfluoroalkyl group; polytetrafluoroethylene (PTFE); tetrafluoroethylene/perfluoro(alkyl vinyl ether) copolymer (PFA); tetrafluoroethylene/hexafluoropropylene copolymer (FEP); tetrafluoroethylene/perfluoro(alkyl vinyl ether)/hexafluoropropylene copolymer (EPA); polyhexafluoropropylene; ethylene/tetrafluoroethylene copolymer (ETFE); poly trifluoroethylene; polyvinylidene fluoride (PVDF); polyvinyl fluoride (PVF); polychlorotrifluoroethylene (PCTFE); ethylene/chlorotrifluoroethylene copolymer (ECTFE); or any combination thereof.

In some embodiments, the passivation layer may comprise magnesium fluoride ($MgF_2$). In some embodiments, the magnesium fluoride of the passivation layer may be a reaction product of a magnesium component present within the 3D article and a fluorine component present in the reactive gas phase. In some embodiments, the magnesium fluoride of the passivation layer may be formed at the surface of the 3D article and below the surface of the 3D article. For example, in some embodiments, the fluorine component may react with at least one of magnesium present at the surface of the 3D article, magnesium present beneath the surface of the 3D article, magnesium that diffuses or migrates from a bulk portion of the 3D article to the surface or an area proximal to the surface, or any combination thereof. In some embodiments, the passivation layer may not be a substantially discrete stratum formed on the surface of the 3D article, but rather may be a region formed at, and optionally beneath, the surface of the 3D article. In some embodiments, the passivation layer is not (and is thus distinct from) a layer applied to a 3D article surface via a coating process or a deposition process (e.g., chemical vapor deposition, atomic layer deposition, physical vapor deposition, etc.). In some embodiments, the term passivation layer may refer to a passivation region at a surface of the 3D article (e.g., formed at and optionally below a surface of the 3D article). In some embodiments, unless otherwise provided, the term passivation layer may be used interchangeably with the term passivation region.

In some embodiments, the passivation layer may comprise, consist of, or consist essentially of at least one of a magnesium compound, a fluoride compound, a magnesium fluoride compound, an oxide compound, a metal compound, a metal oxide compound, or any combination thereof. In some embodiments, the passivation layer may comprise, consist of, or consist essentially of at least one of magnesium fluoride ($MgF_2$), a metal oxide compound, or any combination thereof. In some embodiments, the metal oxide compound may be a reaction product. For example, in some embodiments, the metal oxide compound may be formed upon exposure of the 3D article to oxygen.

In some embodiments, an atomic layer deposition (ALD) coating may optionally be disposed on the passivation layer (e.g., a surface of the passivation layer). In some embodiments, the ALD coating may comprise yttria. In some embodiments, the ALD coating may comprise zirconia. In some embodiments, the ALD coating may comprise titania. In some embodiments, the ALD coating may comprise $AlO_xN_y$, where x is 1 to 5 and N is 1 to 5. In some embodiments, the ALD coating may be on the surface of the 3D article.

In some embodiments, the exposing may be performed at one or more process conditions. The process conditions may comprise at least one of a temperature, a pressure, a duration, or any combination thereof. In addition, the process conditions should be sufficient for the fluorine of the fluorine component to react with the magnesium present within the 3D article to form magnesium fluoride ($MgF_2$). For example, in some embodiments, the process conditions may be a temperature, a pressure, a duration, or any combination thereof sufficient to cause the fluorine of the fluorine component to react with the magnesium present within the 3D article to form $MgF_2$. The process conditions may be varied or adjusted to obtain at least one of a predetermined thickness, a predetermined coverage, a predetermined property (e.g., at least one of corrosion resistance, etch resistance, or any combination thereof), or any combination thereof.

In some embodiments, the exposing is performed at a temperature of 200° C. to 500° C., or any range or subrange therebetween. For example, in some embodiments, the exposing is performed at a temperature of 250° C. to 500° C., 300° C. to 500° C., 350° C. to 500° C., 400° C. to 500° C., 450° C. to 500° C., 200° C. to 400° C., 200° C. to 450° C., 200° C. to 350° C., 200° C. to 300° C., 200° C. to 250° C., 375° C. to 425° C., 375° C. to 450° C., 400° C. to 425° C., 400° C. to 450° C., and/or any range or subrange therebetween.

In some embodiments, the exposing is performed at a pressure of 100 Torr to 1500 Torr, or any range or subrange therebetween. For example, in some embodiments, the exposing is performed at a pressure of 200 Torr to 1500 Torr, 300 Torr to 1500 Torr, 400 Torr to 1500 Torr, 500 Torr to 1500 Torr, 600 Torr to 1500 Torr, 700 Torr to 1500 Torr, 800 Torr to 1500 Torr, 900 Torr to 1500 Torr, 1000 Torr to 1500 Torr, 1100 Torr to 1500 Torr, 1200 Torr to 1500 Torr, 1300 Torr to 1500 Torr, 1400 Torr to 1500 Torr, 100 Torr to 1400 Torr, 100 Torr to 1300 Torr, 100 Torr to 1200 Torr, 100 Torr to 1100 Torr, 100 Torr to 1000 Torr, 100 Torr to 900 Torr, 100 Torr to 800 Torr, 100 Torr to 700 Torr, 100 Torr to 600 Torr, 100 Torr to 500 Torr, 100 Torr to 400 Torr, 100 Torr to 300 Torr, 100 Torr to 200 Torr, 250 Torr to 1000 Torr, 500 Torr to 1000 Torr, 250 Torr to 1250 Torr, 500 Torr to 1250 Torr, and/or any range or subrange therebetween.

In some embodiments, the exposing is performed at a duration of 1 hr to 15 hr, or any range or subrange therebetween. For example, in some embodiments, the exposing is performed at a duration of 2 hr to 13 hr, a duration of 3 hr to 12 hr, and/or any range or subrange therebetween.

In some embodiments, a surface coverage may refer to a percentage of exposed surfaces (e.g., a gas-exposed surface) comprising magnesium fluoride. In some embodiments, the exposed surface(s) may also refer to unmasked surface(s). In some embodiments, the surface coverage may be at least 80% to 100%, or any range or subrange therebetween. For example, in some embodiments, the surface coverage may be at least 90%, at least 91%, at least 92% at least 93%, at least 94%, at least 95%, at least 96%, at least 97%, at least 98%, at least 99%, or 100%. In some embodiments, the surface coverage may range from 80% to 100%, and/or any range or subrange therebetween.

In some embodiments, the passivation layer is a conformal layer. In some embodiments, the passivation layer is a layer having a substantially uniform thickness or a uniform thickness. In some embodiments, the passivation layer may be a corrosion resistant layer or may form a corrosion resistant 3D article surface. In some embodiments, the passivation layer may be an etch resistant layer or may form an etch resistant 3D article surface. In some embodiments, the passivation layer may passivate the surface of the 3D article. In some embodiments, the passivation layer may be a protective layer. In some embodiments, the passivation layer may impart at least one improved surface property.

In some embodiments, the passivation layer may have a thickness of 1 nm to 200 nm, or any range or subrange therebetween. For example, in some embodiments, the passivation layer may have a thickness of 5 nm to 200 nm, 10 nm to 200 nm, 25 nm to 200 nm, 50 nm to 200 nm, 100 nm to 200 nm, 150 nm to 200 nm, 1 nm to 150 nm, 25 nm to 150 nm, 50 nm to 150 nm, 100 nm to 150 nm, 25 nm to 130 nm, 50 nm to 130 nm, 75 nm to 130 nm, and/or any range or subrange therebetween. In some embodiments, the thickness of the passivation layer may be measured by Scanning Electron Microscope (SEM) cross-section, X-ray Photoelectron Spectroscopy (XPS) depth profiling, or Energy Disruptive X-ray Microanalysis (EDAX), among other techniques.

Some embodiments provide articles formed according to any of the methods disclosed herein. For example, in some embodiments, an article may comprise an additive manufactured three-dimensional (3D) body and a passivation layer at a surface of the additive manufactured 3D body. It will be appreciated that the articles may comprise any of the features disclosed herein.

Figure 2:
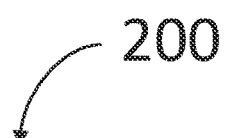
FIG. 2 is a schematic diagram of a cross-section of an article, according to some embodiments of the present disclosure.
Figure 2:
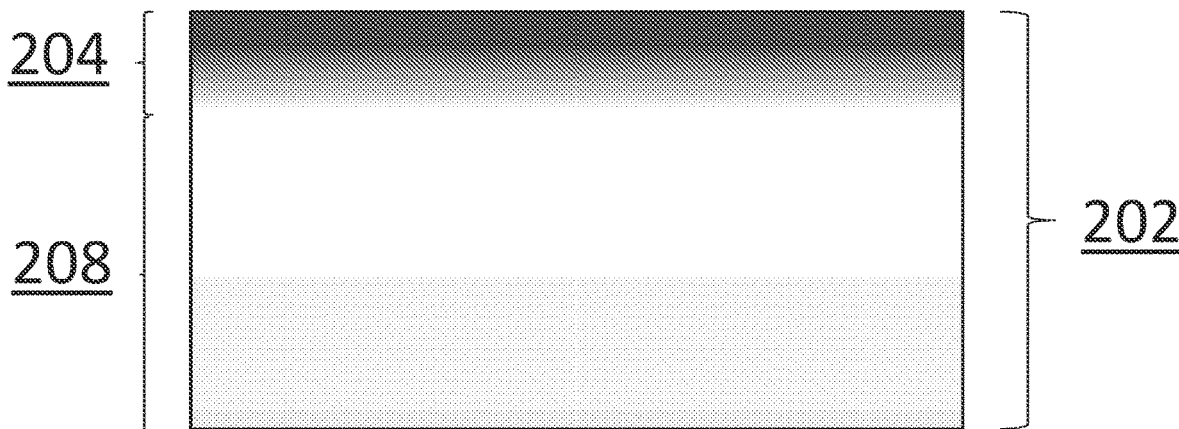

FIG. 2 is a schematic diagram of a cross-section of an article, according to some embodiments of the present disclosure. As shown in FIG. 2, the article 200 may comprise an additive manufactured 3D body 202. The additive manufactured 3D body 202 may comprise a magnesium component. The article 200 may further comprise a passivation layer 204. In some embodiments, the passivation layer 204 may be at and below the surface of the additive manufactured 3D body 202. For example, in some embodiments, the passivation layer 204 may be a passivation region of the additive manufactured 3D body 202 that extends from the surface of the additive manufactured 3D body 202 to a depth within the additive manufactured 3D body 202. In some of these embodiments, the additive manufactured 3D body 202 may further comprise a bulk region 208, wherein the bulk region 208 is a region of the additive manufactured 3D body 202 that is not the region defining the passivation layer 204. In some embodiments, the passivation layer 204 may comprise any surface portion comprising magnesium fluoride. That is, in some embodiments, the magnesium fluoride is a reaction product of the magnesium component and a fluorine component from a reactive gas phase.

The article 200 may have a characteristic of being biocompatible. That is, for example, in some embodiments, the article 200 is biocompatible. As used herein, the term "biocompatible" may refer to a material that is capable of functioning or existing in contact with biological fluid, tissue of a living organism, or any combination thereof, without having a negative effect on the living organism. In some embodiments, the term "biocompatible" refers to a material that is capable of functioning or existing in contact with biological fluid, tissue of a living organism, or any combination thereof, with a net beneficial effect on the living organism. Being biocompatible in some embodiments, the article 200 may be useful as a medical device or a portion of a medical device, among other things.

Accordingly, in some embodiments, the article 200 is a medical device. The medical device may comprise an additive manufactured 3D body and a passivation layer at and below a surface of the additive manufactured 3D body. Any of the additive manufactured 3D bodies and passivation layers of this disclosure may be used herein. For example, in some embodiments, the additive manufactured 3D body comprises a magnesium component. In some embodiments, the passivation layer comprises magnesium fluoride. In some embodiments, the magnesium fluoride is a reaction product of the magnesium component and a fluorine component from a reactive gas phase.

In some embodiments, the medical device is configured for implantation into a mammal. In some embodiments, the medical device is configured for temporary insertion into a mammal. In some embodiments, the medical device is configured for external use on a mammal. In some embodiments, the additive manufactured 3D body is biocompatible. In some embodiments, the additive manufactured 3D body is a body of the medical device. In some embodiments, the additive manufactured 3D body is a component of the medical device.

In some embodiments, the additive manufactured 3D body is at least one of a balloon, a graft, a stent, a catheter, a shunt, an embolic agent, a pacemaker, a defibrillator, an artificial implant, a prosthetic, a stimulator, a sensor, a wire, a lead, a valve, a plug, a pump, a filter, a mechanical connector, a tube, a plate, a surgical tool, an enclosure, any component thereof, or any combination thereof. In some embodiments, the additive manufactured 3D body is at least one of an angioplasty balloon, a valvuloplasty balloon, a deployment balloon, a pacemaker lead, a prosthetic heart valve, a vascular filter, a vascular plug, an artificial heart valve, an artificial heart, a catheter tip, a suture, a surgical staple, a screw, a nail, a bracket, a pin, a rod, a fixture, a guide wire, a drug pump, a synthetic vessel graft, a vascular graft, a nonvascular graft, a stent graft, a vascular stent, a coronary stent, a peripheral stent, an intraluminal paving stent, an arteriovenous shunt, an aneurysm filler, an implantable pulse generator, an implantable cardiac defibrillator, a cardioverter defibrillator, a spinal stimulator, a brain stimulator, a sacral nerve stimulator, a bone prosthetic, a joint prosthetic, a plastic tubing, a metal tubing, a dental braces, a hearing aid, a bandage, any component thereof, or any combination thereof.

In some embodiments, the additive manufactured 3D body comprises a structure having an aspect ratio of 2:1 to 1000:1. In some embodiments, the aspect ratio is a ratio of two of a width, a depth, a height, or a diameter.

In some embodiments, the magnesium component comprises at least one of a magnesium-containing metal alloy, a magnesium ion, a magnesium-containing metal oxide, elemental magnesium, or any combination thereof.

In some embodiments, the additive manufactured 3D body has a monolithic structure that is not capable of construction by machining. In some embodiments, the additive manufactured 3D body is an article of unitary construction. In some embodiments, the additive manufactured 3D body does not comprise seams. In some embodiments, the additive manufactured 3D body does not comprise braze joints. In some embodiments, the additive manufactured 3D body does not comprise weld joints.

In some embodiments, the reactive gas phase comprises at least one of $CF_4$, $C_2F_4$, $C_3F_6$, $C_4F_8$, $CHF_3$, $C_2H_2F_2$, $C_2F_6$, HF, $CH_3F$, or any combination thereof. In some embodiments, the reactive gas phase is derived from at least one of polymerized perfluoroalkylethylene having a $C_1$-$C_{10}$ perfluoroalkyl group; polytetrafluoroethylene (PTFE); tetrafluoroethylene/perfluoro(alkyl vinyl ether) copolymer (PFA); tetrafluoroethylene/hexafluoropropylene copolymer (FEP); tetrafluoroethylene/perfluoro(alkyl vinyl ether)/hexafluoropropylene copolymer (EPA); polyhexafluoropropylene; ethylene/tetrafluoroethylene copolymer (ETFE); poly trifluoroethylene; polyvinylidene fluoride (PVDF); polyvinyl fluoride (PVF); polychlorotrifluoroethylene (PCTFE); ethylene/chlorotrifluoroethylene copolymer (ECTFE); or any combination thereof.

Figure 3:
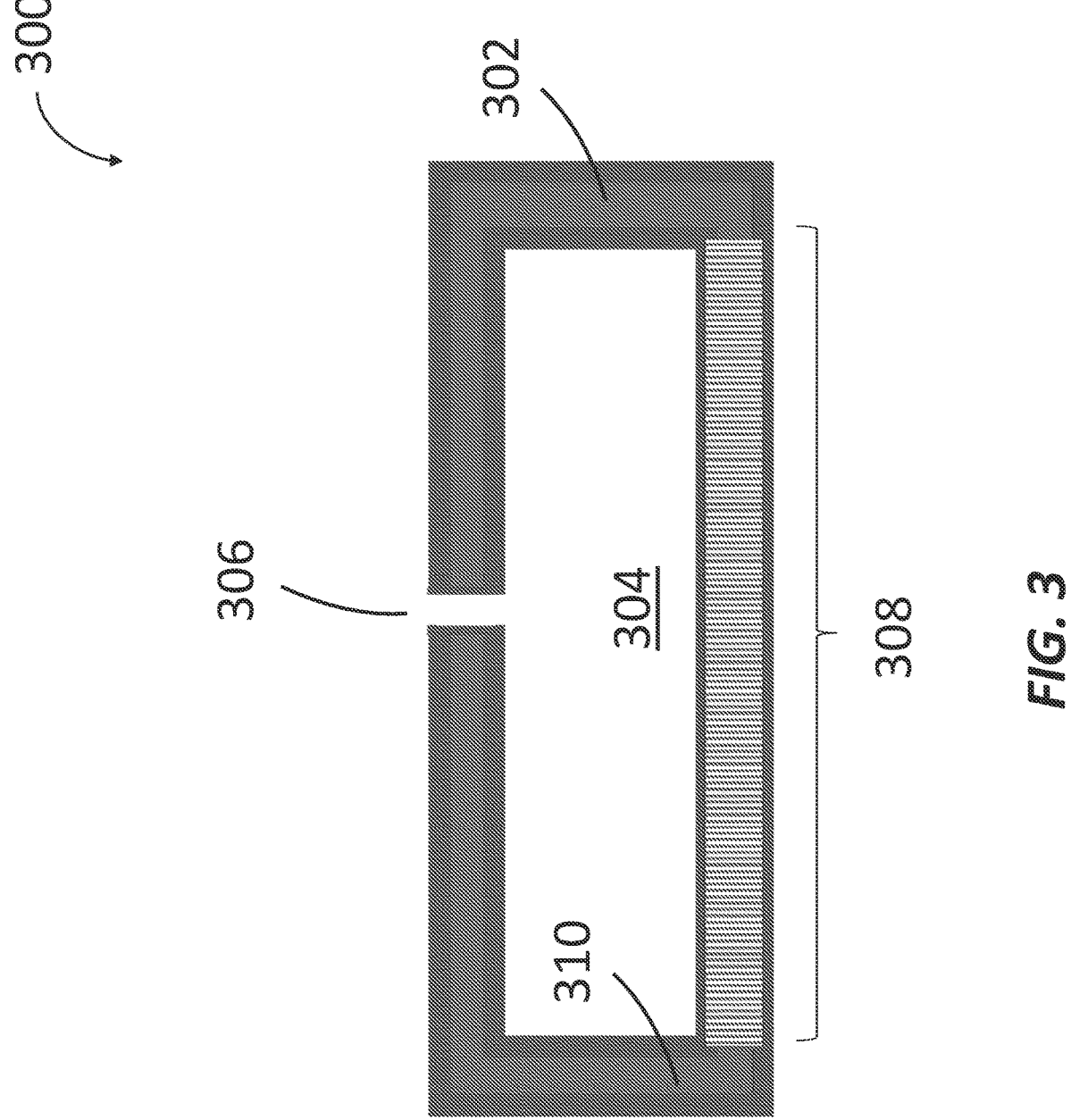
FIG. 3 is a schematic diagram of a cross-section of an article, according to some embodiments of the present disclosure.

FIG. 3 is a schematic diagram of an article, according to some embodiments of the present disclosure. In some embodiments, the article 300 may be a component (e.g., a structure, a material, an apparatus, an equipment, etc.) used in semiconductor or microelectronic fabrication apparatuses, systems, components, parts, equipment, or processes. In some embodiments, the article 300 is a showerhead used to provide a processing gas onto a semiconductor wafer inside a process chamber. As shown in FIG. 3, the article 300 may comprise an additive manufactured 3D support structure 302 forming a cavity 304. In some embodiments, an opening 306 is formed in the cavity 304. In some embodiments, one or more process gases may flow through the opening 306 into the cavity 304. In some embodiments, the additive manufactured 3D support structure 302 further comprises a plurality of holes 308 through which the one or more process gases flow. As shown in FIG. 3, the shower head component may comprise a passivation layer 310. In some embodiments, the passivation layer 310 is formed on all exposed surfaces of the shower head component.

Example 1

$MgF_2$-Passivated Aluminum-Containing Additive Manufactured Articles

Figure 4:
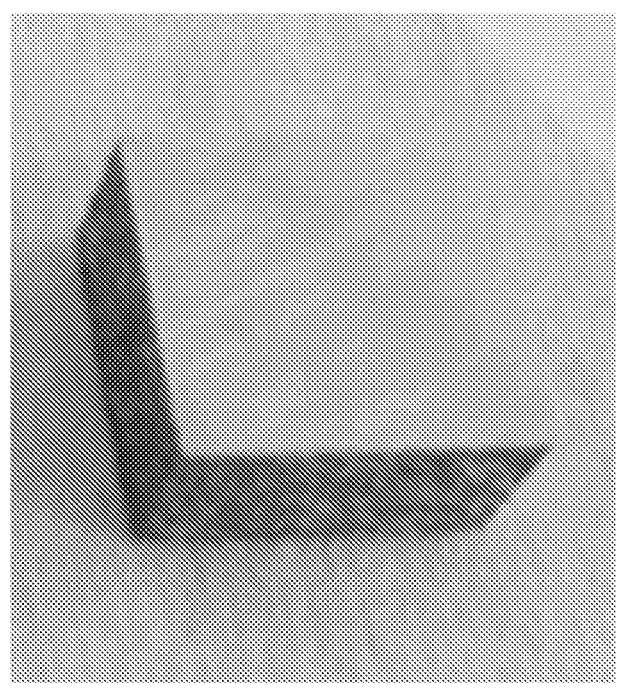
FIG. 4 is an image of an additive manufactured article before passivating a surface of the additive manufactured article, according to some embodiments of the present disclosure.
Figure 5:
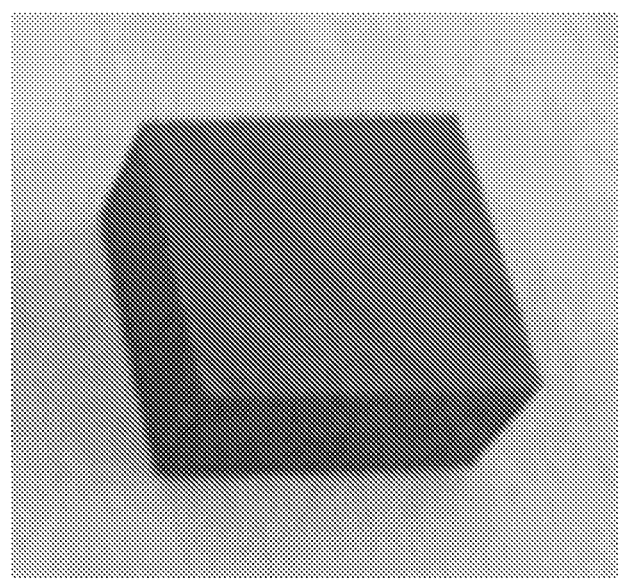
FIG. 5 is an image of the additive manufactured article from FIG. 4 after passivating the surface of the additive manufactured article, according to some embodiments of the present disclosure.

FIGS. 4-5 are images of an additive manufactured article prior to a surface of the additive manufactured article being passivated, which is presented in FIG. 4, and following passivation of the surface of the additive manufactured article, which is presented in FIG. 5, according to some embodiments of the present disclosure. The additive manufactured articles of FIGS. 4-5 comprise aluminum. In FIG. 5, the passivation layer is shown as having a darker surface than the unpassivated surface of the article presented in FIG. 4.

Figure 6:
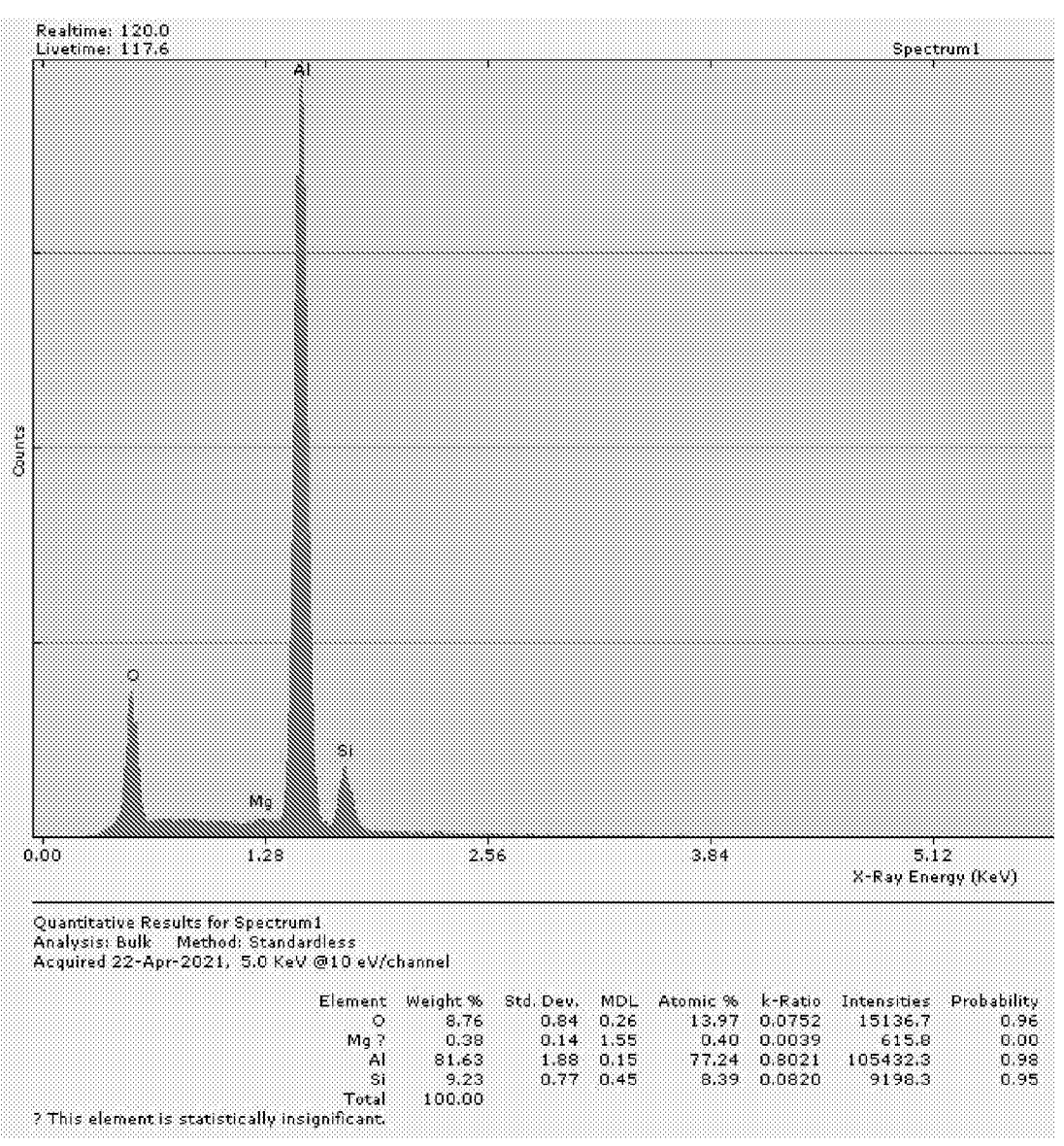
FIG. 6 is a graphical view of an energy dispersive X-ray spectroscopy (EDS), according to some embodiments of the present disclosure.
Figure 7:
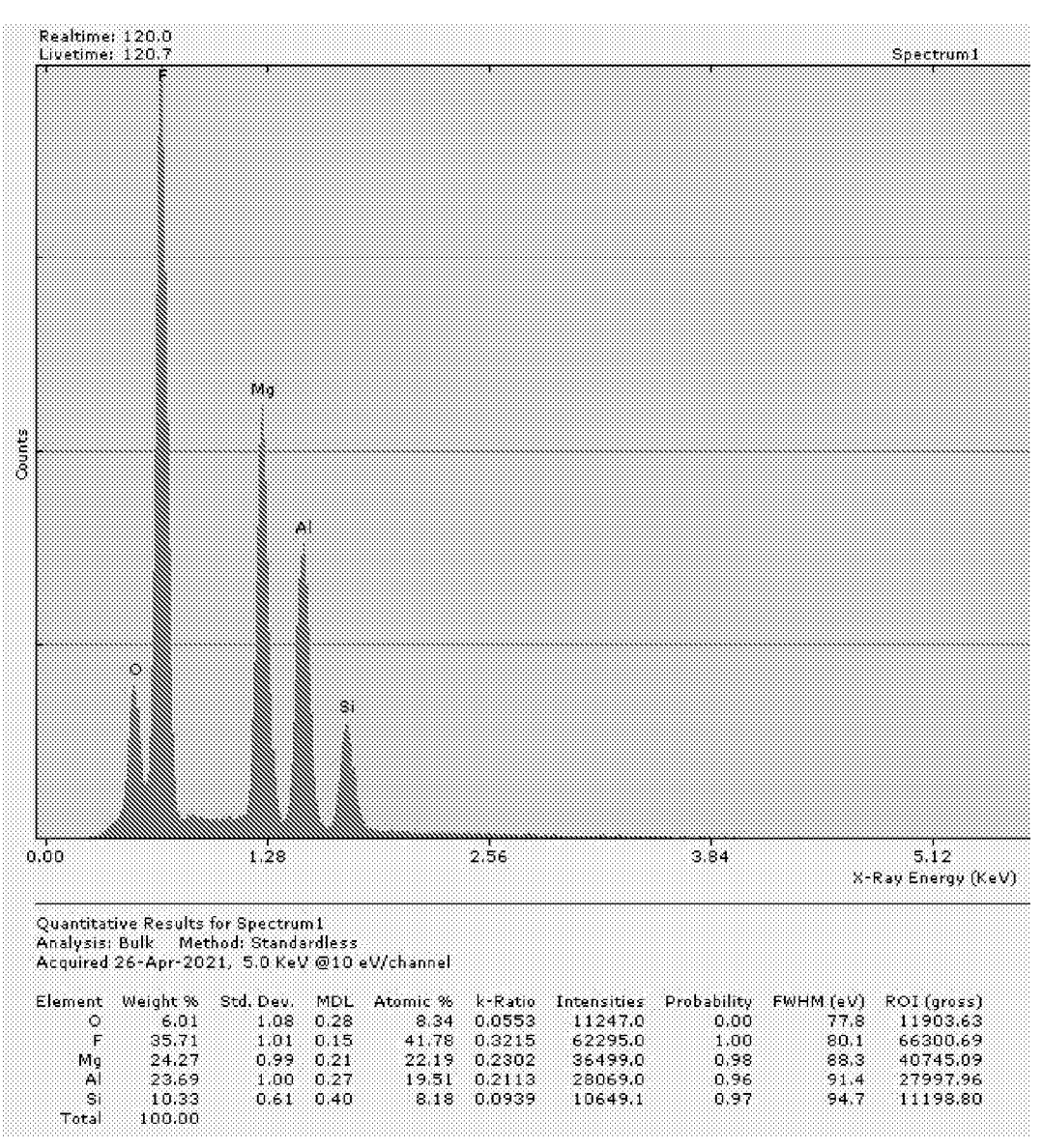
FIG. 7 is a graphical view of an energy dispersive X-ray spectroscopy (EDS), according to some embodiments of the present disclosure.

FIGS. 6-7 are graphical views of energy dispersive X-ray spectroscopy (EDS) showing the elemental spectra for a probing depth of approximately 250 nm, according to some embodiments of the present disclosure. The EDS spectra of FIGS. 6-7 correspond to the additive manufactured articles presented in FIGS. 4-5, respectively. In FIG. 6, the peak corresponding to fluorine is not detected and the peak corresponding to magnesium is low. In comparison to FIG.

6, and as shown in FIG. 7, the EDS detected both magnesium and fluoride in the region from the surface of the additive manufactured article to the probing depth, confirming the formation of magnesium fluoride. The increase in magnesium in comparison to FIG. 6 is the result of magnesium diffusing from the bulk of the additive manufactured article to the surface during the formation of the passivation layer. In some embodiments, a thickness of the magnesium fluoride surface layer was measured to be about 100 nm.

What is claimed is:

1. A method for forming an article comprising: forming a three-dimensional (3D) article by additive manufacturing to obtain an additive manufactured 3D article, wherein the additive manufactured 3D article comprises a magnesium component; and exposing the additive manufactured 3D article to a reactive gas phase to form a passivation layer, wherein the reactive gas phase comprises a fluorine component, wherein the fluorine component reacts with the magnesium component to form magnesium fluoride at and below a surface of the additive manufactured 3D article, and wherein the magnesium fluoride covers at least 90% of gas-exposed surfaces of the additive manufactured 3D article.

2. The method according to claim 1, wherein the forming comprises dispensing a 3D printable material from a 3D printer to form the additive manufactured 3D article.

3. The method according to claim 1, wherein the magnesium component comprises at least one of a magnesium-containing metal alloy, a magnesium ion, a magnesium-containing metal oxide, elemental magnesium, or any combination thereof.

4. The method according to claim 1, wherein the additive manufactured 3D article has a monolithic structure that is not capable of construction by machining.

5. The method according to claim 1, wherein the additive manufactured 3D article is an article of unitary construction.

6. The method according to claim 1, wherein the additive manufactured 3D article comprises at least one of a plenum, a trench, a structure defining a hole, a structure defining a channel, a structure defining a cavity, or any combination thereof.

7. The method according to claim 1, wherein the additive manufactured 3D article has an aspect ratio of 2:1 to 1000:1, wherein the aspect ratio is a ratio of two of a width, a depth, a height, or a diameter.

8. The method according to claim 1, wherein the additive manufactured 3D article does not comprise seams.

9. The method according to claim 1, wherein the additive manufactured 3D article does not comprise braze joints.

10. The method according to claim 1, wherein the additive manufactured 3D article does not comprise weld joints.

11. The method according to claim 1, wherein the reactive gas phase comprises at least one of $CF_4$, $C_2F_4$, $C_3F_6$, $C_4F_8$, $CHF_3$, $C_2H_2F_2$, $C_2F_6$, HF, $CH_3F$, or any combination thereof.

12. The method according to claim 1, wherein the reactive gas phase is derived from at least one of polymerized perfluoroalkylethylene having a $C_1$-$C_{10}$ perfluoroalkyl group; polytetrafluoroethylene (PTFE); tetrafluoroethylene/perfluoro (alkyl vinyl ether) copolymer (PFA); tetrafluoroethylene/hexafluoropropylene copolymer (FEP); tetrafluoroethylene/perfluoro (alkyl vinyl ether)/hexafluoropropylene copolymer (EPA); polyhexafluoropropylene; ethylene/tetrafluoroethylene copolymer (ETFE); poly trifluoroethylene; polyvinylidene fluoride (PVDF); polyvinyl fluoride (PVF); polychlorotrifluoroethylene (PCTFE); ethylene/chlorotrifluoroethylene copolymer (ECTFE); or any combination thereof.

13. The method of claim 1, wherein the article is a medical device.

* * * * *